(12) United States Patent
Kim et al.

(10) Patent No.: US 10,471,410 B2
(45) Date of Patent: Nov. 12, 2019

(54) METHOD FOR PREPARING SUPERABSORBENT POLYMER WITH IMPROVED ANTI-CAKING

(71) Applicant: LG Chem, Ltd., Seoul (KR)

(72) Inventors: Su-Jin Kim, Daejeon (KR); Young Sam Kim, Daejeon (KR); Bo-Hee Park, Daejeon (KR); Young-In Yang, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/766,656

(22) PCT Filed: Jan. 31, 2017

(86) PCT No.: PCT/KR2017/001024
§ 371 (c)(1),
(2) Date: Apr. 6, 2018

(87) PCT Pub. No.: WO2017/142230
PCT Pub. Date: Aug. 24, 2017

(65) Prior Publication Data
US 2018/0297012 A1    Oct. 18, 2018

(30) Foreign Application Priority Data

Feb. 17, 2016  (KR) .................. 10-2016-0018525

(51) Int. Cl.
| | | |
|---|---|---|
| *B01J 20/26* | (2006.01) |
| *C08J 3/205* | (2006.01) |
| *C08K 3/36* | (2006.01) |
| *C08K 3/30* | (2006.01) |
| *C08K 5/053* | (2006.01) |
| *C08K 5/092* | (2006.01) |
| *A61L 15/18* | (2006.01) |
| *A61L 15/26* | (2006.01) |
| *A61L 15/42* | (2006.01) |
| *A61L 15/60* | (2006.01) |
| *B01J 20/02* | (2006.01) |
| *B01J 20/10* | (2006.01) |
| *B01J 20/22* | (2006.01) |
| *B01J 20/28* | (2006.01) |
| *B01J 20/30* | (2006.01) |
| *C08F 220/06* | (2006.01) |
| *C08L 33/02* | (2006.01) |

(52) U.S. Cl.
CPC ............ *B01J 20/267* (2013.01); *A61L 15/18* (2013.01); *A61L 15/26* (2013.01); *A61L 15/425* (2013.01); *A61L 15/60* (2013.01); *B01J 20/0248* (2013.01); *B01J 20/0281* (2013.01); *B01J 20/103* (2013.01); *B01J 20/22* (2013.01); *B01J 20/28004* (2013.01); *B01J 20/28007* (2013.01); *B01J 20/28016* (2013.01); *B01J 20/28061* (2013.01); *B01J 20/28064* (2013.01); *B01J 20/28066* (2013.01); *B01J 20/3042* (2013.01); *B01J 20/3085* (2013.01); *C08F 220/06* (2013.01); *C08J 3/205* (2013.01); *C08K 3/30* (2013.01); *C08K 3/36* (2013.01); *C08K 5/053* (2013.01); *C08K 5/092* (2013.01); *C08L 33/02* (2013.01); *C08J 2333/02* (2013.01); *C08K 2003/3081* (2013.01); *C08K 2201/006* (2013.01)

(58) Field of Classification Search
CPC ..................................................... B01J 20/267
See application file for complete search history.

(56) References Cited

U.S. PATENT DOCUMENTS

| | | | |
|---|---|---|---|
| 4,771,105 | A | 9/1988 | Shirai et al. |
| 5,164,459 | A | 11/1992 | Kimura et al. |
| 2006/0204755 | A1 | 9/2006 | Torii et al. |
| 2008/0032888 | A1 | 2/2008 | Nakamura et al. |
| 2008/0221237 | A1 | 9/2008 | Herfert et al. |
| 2009/0215617 | A1 | 8/2009 | Kimura et al. |
| 2009/0298685 | A1 | 12/2009 | Torii et al. |
| 2010/0130355 | A1 | 5/2010 | Tian et al. |
| 2012/0220733 | A1 | 8/2012 | Machida et al. |
| 2013/0026412 | A1 | 1/2013 | Machida et al. |
| 2013/0130895 | A1 | 5/2013 | Herfert et al. |
| 2013/0260988 | A1 | 10/2013 | Herfert et al. |
| 2015/0299404 | A1 | 10/2015 | Daniel et al. |
| 2016/0199527 | A1 | 7/2016 | Ota et al. |
| 2016/0235882 | A1 | 8/2016 | Noh et al. |

(Continued)

FOREIGN PATENT DOCUMENTS

| | | |
|---|---|---|
| EP | 2479195 A1 | 7/2012 |
| EP | 2557095 A1 | 2/2013 |

(Continued)

OTHER PUBLICATIONS

Third Party Observation in PCT Application No. PCT/KR2017/001024 submitted by Anonymous Jun. 15, 2018 and dated Jun. 20, 2018.

(Continued)

*Primary Examiner* — Peter F Godenschwager

(74) *Attorney, Agent, or Firm* — Lerner, David, Littenberg, Krumholz & Mentlik, LLP

(57) ABSTRACT

The present invention relates to a method for preparing superabsorbent polymer with improved anti-caking, and according to the present invention, a method for preparing superabsorbent polymer that has properties equivalent to or more excellent than the existing superabsorbent polymer but has improved anti-caking, and thus, has excellent processability, and superabsorbent polymer prepared thereby, are provided.

19 Claims, 5 Drawing Sheets

(56) References Cited

U.S. PATENT DOCUMENTS

| | | |
|---|---|---|
| 2016/0271584 A1 | 9/2016 | Lee et al. |
| 2017/0050171 A1 | 2/2017 | Yang et al. |
| 2017/0173563 A1 | 6/2017 | Kim et al. |
| 2017/0233534 A1* | 8/2017 | Kim .................. C08J 3/075 524/556 |

FOREIGN PATENT DOCUMENTS

| | | |
|---|---|---|
| EP | 3078679 A1 | 10/2016 |
| EP | 3309195 A1 | 4/2018 |
| EP | 3321306 A1 | 5/2018 |
| JP | 2003306609 A | 10/2003 |
| JP | 2004512165 A | 4/2004 |
| JP | 2008142714 A | 6/2008 |
| JP | 2008528752 A | 7/2008 |
| JP | 5183897 B2 | 4/2013 |
| JP | 2014079324 A | 5/2014 |
| KR | 940000965 B1 | 2/1994 |
| KR | 0143403 B1 | 7/1998 |
| KR | 20110096052 A | 8/2011 |
| KR | 20120081113 A | 7/2012 |
| KR | 101507287 B1 | 3/2015 |
| KR | 20150064649 A | 6/2015 |
| KR | 20150069320 A | 6/2015 |
| KR | 20150087368 A | 7/2015 |
| KR | 20160076559 A | 7/2016 |
| KR | 20160145424 A | 12/2016 |
| WO | 2005108472 A1 | 11/2005 |
| WO | 2007037522 A1 | 4/2007 |
| WO | 2007116777 A1 | 10/2007 |
| WO | 2015084060 A1 | 6/2015 |

OTHER PUBLICATIONS

International Search Report for Application No. PCT/KR2017/001024 dated May 4, 2017.

Extended European Search Report including Written Opinion for Application No. EP17753391.6 dated Oct. 15, 2018.

* cited by examiner

METHOD FOR PREPARING SUPERABSORBENT POLYMER WITH IMPROVED ANTI-CAKING

CROSS-REFERENCE TO RELATED APPLICATIONS

The present application is a national phase entry under 35 U.S.C. § 371 of International Application No. PCT/KR2017/001024, filed on Jan. 31, 2017, which claims the benefit of Korean Patent Application No. 10-2016-0018525 filed on Feb. 17, 2016 with the Korean Intellectual Property Office, the disclosures of which are herein incorporated by reference.

BACKGROUND OF THE INVENTION (a) Field of the Invention

The present invention relates to a method for preparing superabsorbent polymer with improved anti-caking.

(b) Description of the Related Art

Super absorbent polymers (SAPs) are synthetic polymer materials that can absorb moisture of 500 to 1000 times of self-weight. Such superabsorbent polymer is frequently used for hygienic goods such as diapers for children, diapers for adults, etc., due to its excellent water absorption, and when applied for hygienic goods, it performs functions for absorbing and maintaining urine existing in a diaper.

In this regard, the prior art including Korean Patent Laid-Open Publication No. 2012-0081113, etc. discloses a preparation method of superabsorbent polymer comprising water-insoluble inorganic fine particles, but according to such a technology, since increase in the moisture on the surface of superabsorbent polymer causes increase in the viscosity of the surface, problems of agglomeration, decrease in processability and productivity, etc. may be generated, and thus, it was difficult to simultaneously satisfy high moisture content and high processability.

Therefore, there is a demand for the development of superabsorbent polymer that can be uniformly hydrated without agglomeration and caking of the superabsorbent polymer particles, and thus, has excellent processability and properties, and a method for preparing the same.

SUMMARY OF THE INVENTION

In order to solve the problems of the prior art, it is an object of the present invention to provide a method for preparing superabsorbent polymer with improved anti-caking, wherein the surface of the superabsorbent polymer is modified, and thus, viscosity and cohesion are not increased by water absorption, and ultimately, caking between superabsorbent polymer particles are basically blocked during the storage and transfer as a product, and processability is not decreased.

It is another object of the present invention to provide superabsorbent polymer with improved anti-caking, prepared by the above preparation method.

In order to achieve the object, the present invention provides a method for preparing superabsorbent polymer with improved anti-caking, comprising the steps of:

a) introducing
water, and
two or more selected from the group consisting of particles having i) a BET specific surface area of 300 to 1500 $m^2/g$, and ii) a porosity of 50% or more, multivalent metal salts, organic acid and polyhydric alcohol into superabsorbent polymer to prepare hydrated superabsorbent polymer; and b) aging the superabsorbent polymer prepared in the step a).

According to the present invention, superabsorbent polymer that has properties equivalent to or more excellent than the existing superabsorbent polymer but has improved anti-caking, and thus, has excellent processability because caking of particles is prevented, can be provided.

DETAILED DESCRIPTION OF THE EMBODIMENTS

Figure 1:
FIG. 1 is a photograph showing the shape of superabsorbent polymer according to Example 1 that remains in a petri dish after conducting step 3) during the anti-caking test of Experimental Example 1.
Figure 2:
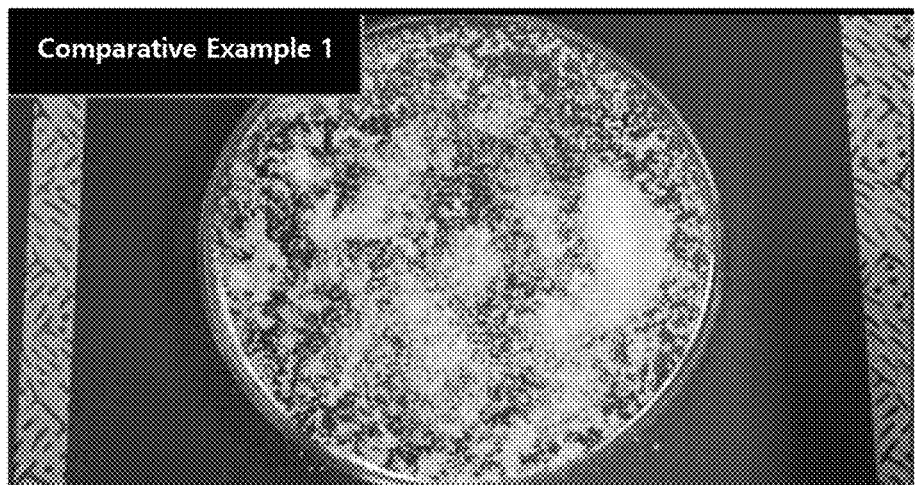
FIG. 2 is a photograph showing the shape of superabsorbent polymer according to Comparative Example 1 that remains in a petri dish after conducting step 3) during the anti-caking test of Experimental Example 1.
Figure 3:
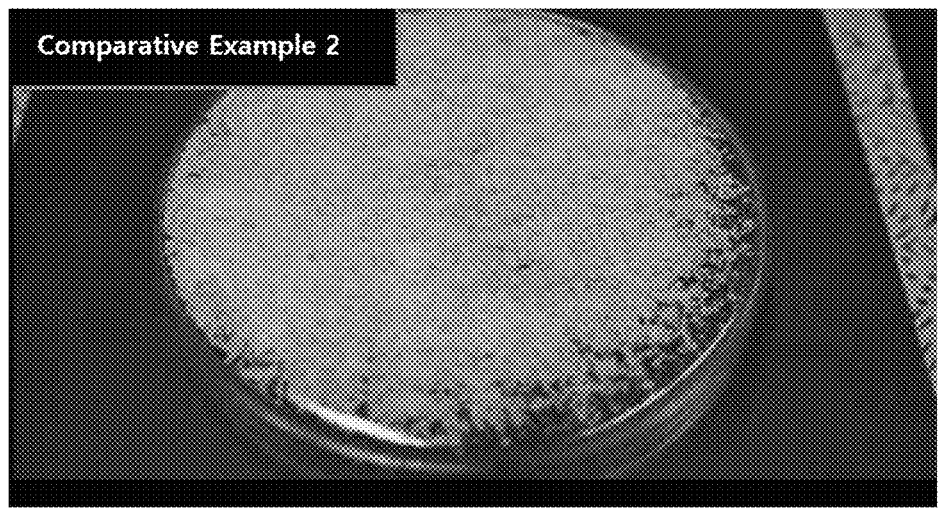
FIG. 3 is a photograph showing the shape of superabsorbent polymer according to Comparative Example 2 that remains in a petri dish after conducting step 3) during the anti-caking test of Experimental Example 1.
Figure 4:
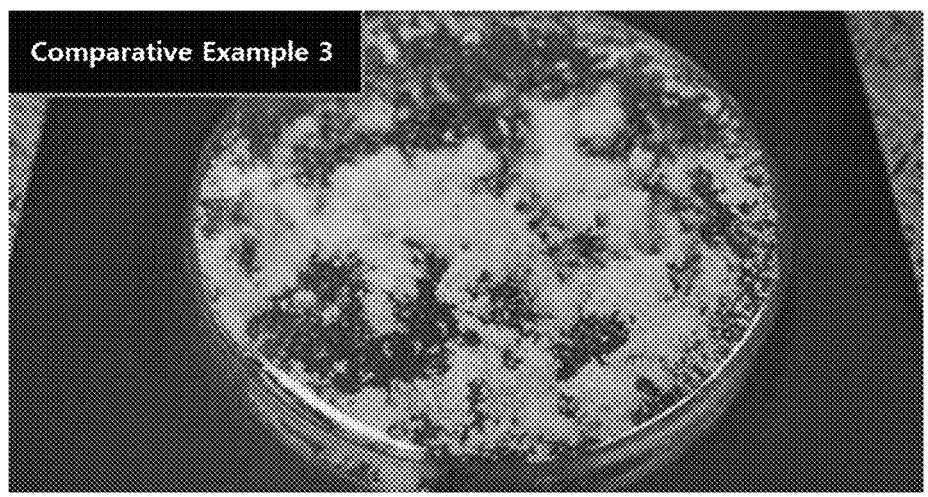
FIG. 4 is a photograph showing the shape of superabsorbent polymer according to Comparative Example 3 that remains in a petri dish after conducting step 3) during the anti-caking test of Experimental Example 1.
Figure 5:
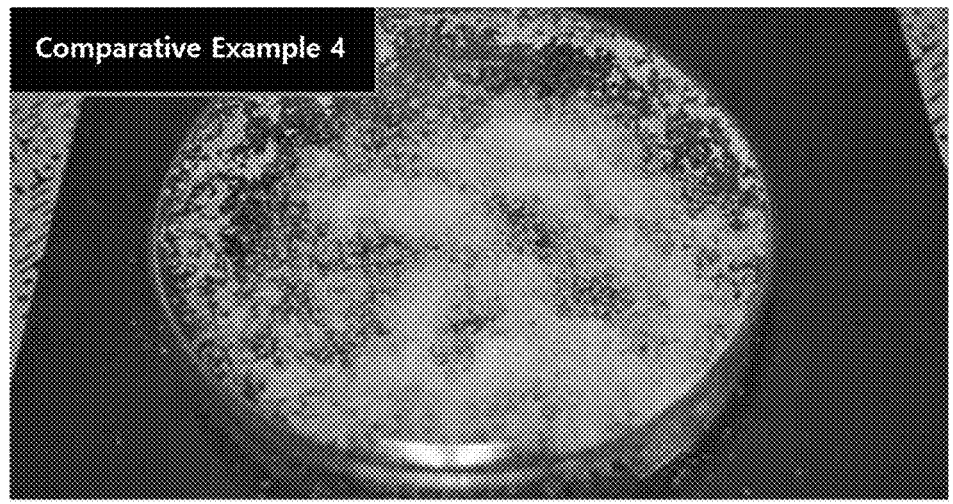
FIG. 5 is a photograph showing the shape of superabsorbent polymer according to Comparative Example 4 that remains in a petri dish after conducting step 3) during the anti-caking test of Experimental Example 1.
Figure 6:
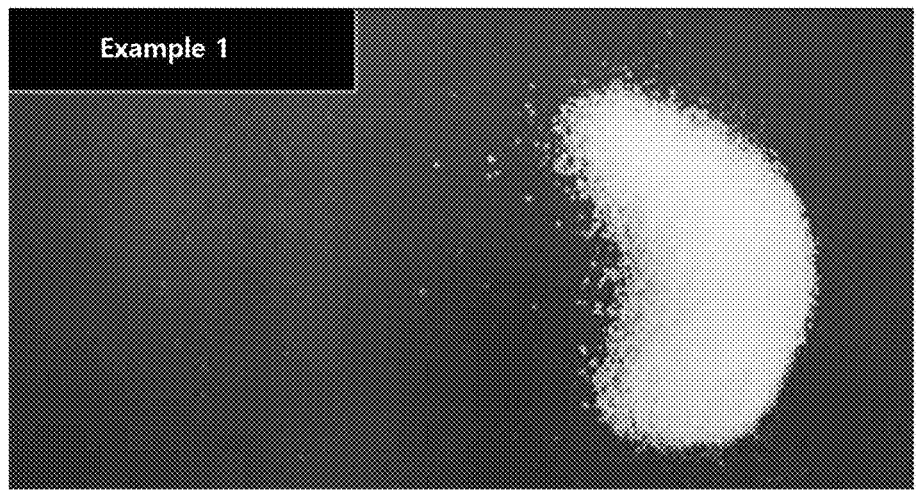
FIG. 6 is a photograph showing the shape of superabsorbent polymer according to Example 1 that is separated from a petri dish after conducting step 5) during the anti-caking test of Experimental Example 1.
Figure 7:
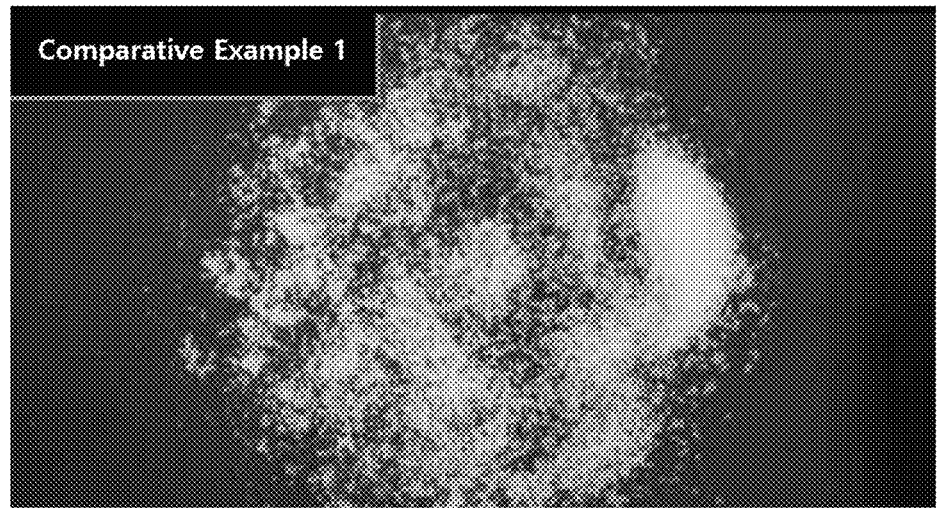
FIG. 7 is a photograph showing the shape of superabsorbent polymer according to Comparative Example 1 that is separated from a petri dish after conducting step 5) during the anti-caking test of Experimental Example 1.
Figure 8:
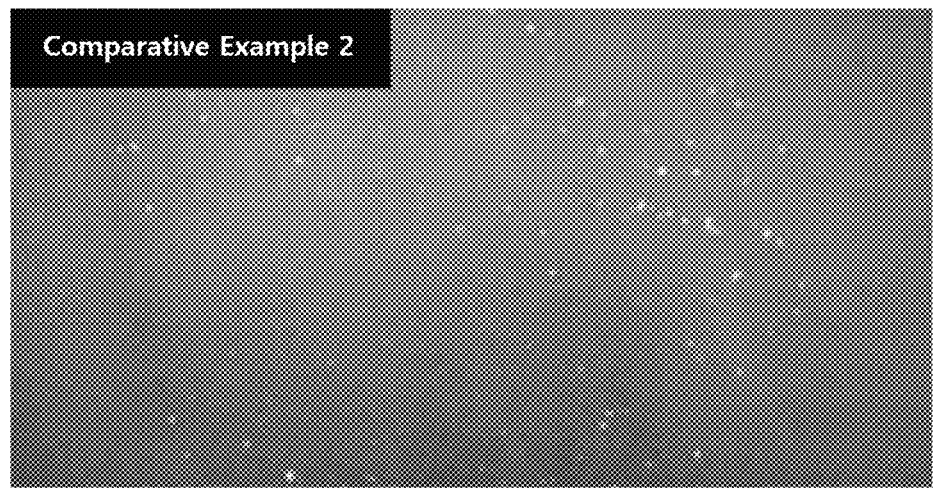
FIG. 8 is a photograph showing the shape of superabsorbent polymer according to Comparative Example 2 that is separated from a petri dish after conducting step 5) during the anti-caking test of Experimental Example 1.
Figure 9:
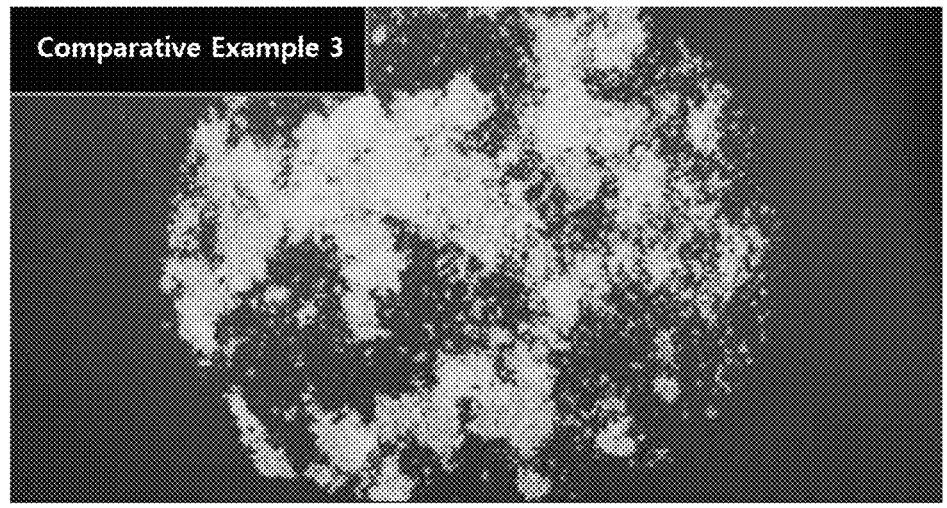
FIG. 9 is a photograph showing the shape of superabsorbent polymer according to Comparative Example 3 that is separated from a petri dish after conducting step 5) during the anti-caking test of Experimental Example 1.
Figure 10:
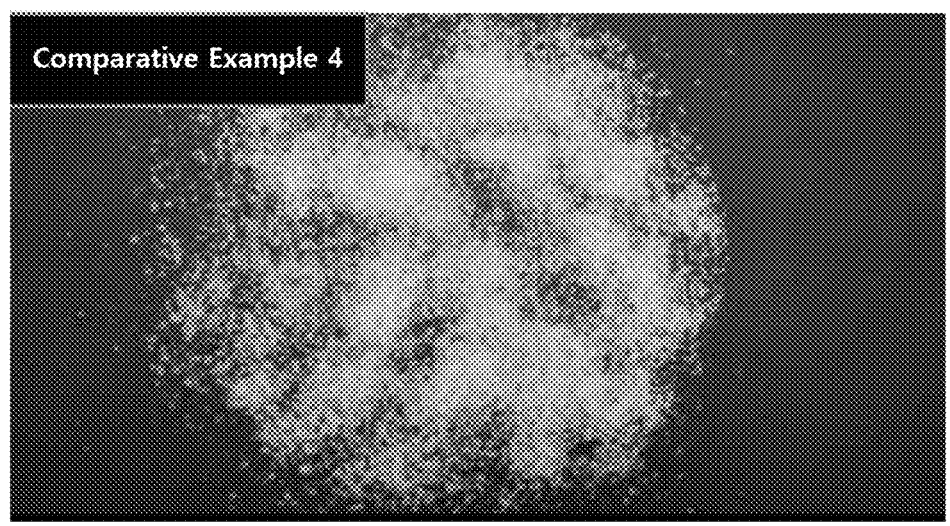
FIG. 10 is a photograph showing the shape of superabsorbent polymer according to Comparative Example 4 that is separated from a petri dish after conducting step 5) during the anti-caking test of Experimental Example 1.

Hereinafter, the present invention will be explained in detail.

The present invention relates to a method for preparing superabsorbent polymer with improved anti-caking, comprising the steps of:

a) introducing
water, and
two or more selected from the group consisting of particles having i) a BET specific surface area of 300 to 1500 $m^2/g$, and ii) a porosity of 50% or more, multivalent metal salts, organic acid and polyhydric alcohol into superabsorbent polymer to prepare hydrated superabsorbent polymer; and b) aging the superabsorbent polymer prepared in the step a).

According to one embodiment of the present invention, the step of aging may be conducted using an appropriate stirrer.

According to another embodiment of the present invention, the step of aging may be preferably conducted at a speed of 5~1500 rpm so as to prevent caking during the process of introducing water into the superabsorbent polymer to the process of packaging, but the speed is not limited thereto.

According to still one embodiment of the present invention, the step of aging may be conducted at 26 to 95° C., and in case the aging is conducted within the above temperature range, the degree of caking between particles after introducing water into the superabsorbent polymer may decrease, thus shortening the process time, and the process may be simplified. If the aging is conducted below 26° C., the process time may too lengthen, and if it is conducted above 95° C., the absorption speed of superabsorbent polymer may increase, and thus, water may be evaporated or it may be difficult to uniformly increase moisture content.

According to another embodiment of the present invention, the step of aging may be preferably conducted for 1 to 120 minutes so as to prevent caking during the process of introducing water into the superabsorbent polymer to the process of packaging, but the aging time is not limited thereto. If the aging time is shorter than the above range, caking between particles may be generated, and if the aging time is longer than the above range, it may not be economical due to unnecessary process.

According to one embodiment of the present invention, it is preferable that the particles are included in the content of 0.0001 to 15 parts by weight, more preferably 0.001 to 2.0 parts by weight, and most preferably 0.05 to 0.15 parts by weight, based on 100 parts by weight of the superabsorbent polymer.

If the content of the particles is less than the above range, it is not sufficient to obtain expected effect, and if it is greater than the above range, the particles may be excessively used, which is not economical.

In general, the surface of superabsorbent polymer is hydrophilic, and when dried after absorbing water, irreversible agglomeration is generated by capillary force by water existing between particles, hydrogen bond, inter-particular diffusion or van der Waals force between particles, etc. Thus, water is necessarily used during the polymerization of superabsorbent polymer and surface crosslinking, which generates agglomeration, thus increasing internal load, and consequently, causing equipment failure. And, since the particle size of the agglomerated superabsorbent polymer is large, which is not appropriate for melting, a disintegration process for reducing the particles size to an optimal particle size should be introduced. And, since a strong force is applied during the disintegration process, the crushing of superabsorbent polymer may cause property degeneration.

In order to solve the problem, there was an attempt to introduce various fine particles that exist on the surface of superabsorbent polymer and can hinder the direct agglomeration of polymer particles, but in case an excessive amount of fine particles are introduced, although agglomeration is prevented, absorption under load of superabsorbent polymer may decrease.

In order to solve the problem, the particles introduced into the superabsorbent polymer of the present invention have a particle size of 2 nm to 50 µm. And, the particles may have a BET specific surface area of 300 to 1500 m$^2$/g, preferably 500 to 1500 m$^2$/g, more preferably 600 to 1500 m$^2$/g. And, the fine particles may have super hydrophobicity with a water contact angle of 125° or more, preferably 135° or more, more preferably 140° or more. And, the particles may have a particle size of 2 nm to 50 µm and super hydrophobicity with a water contact angle of 125° or more.

And, the particles may have a porosity of 50% or more, preferably 90% or more. Since the superabsorbent polymer of the present invention uses particles having the above properties, the influence of water on the surface of the polymer may be decreased. In addition, since fine particles having porosity and super hydrophobicity are used, agglomeration may be remarkably decreased, and even if relatively a small amount of fine particles are used, penetration may be easily improved, and absorption under load may be easily maintained.

The particles added in the preparation method of superabsorbent polymer with improved anti-caking according to the present invention are not limited in terms of the constructions as long as they have the above properties, and specifically, inorganic oxide such as silica ($SiO_2$), alumina, titania ($TiO_2$), carbon, etc., inorganic compounds, organic polymer, ion exchange resin, metal, metal salts, etc. may be used, but not limited thereto, and preferably, silica ($SiO_2$) is used.

And, as the process of adding the particles, the particles may be dispersed in a monomer solution and then used, or may be added to hydrogel after polymerization and then dry mixed with first dried polymer particles, or may be dispersed in water or organic solvents in which a surface crosslinking solution is dissolved and then mixed during surface crosslinking, or may be separated from water or organic solvents in which a surface crosslinking solution is dissolved and dry mixed during surface crosslinking, or may be dry mixed with the surface crosslinked final product, etc., but not limited thereto.

According to another embodiment of the present invention, water is preferably included in the content of 0.1 to 20.0 parts by weight, more preferably 1.0 to 10.0 parts by weight, and most preferably 2.5 to 7.5 parts by weight, based on 100 parts by weight of the superabsorbent polymer and particles.

If the content of water is less than the above range, it may not be sufficient to obtain anti-caking, and if it is greater than the above range, stickiness of the polymer surface may increase, and irreversible agglomeration between the superabsorbent polymer particles may be generated, and thus, processability of polymer may decrease and particle size may be changed, thus rendering it difficult to use as a product.

In the preparation process superabsorbent polymer, water is a polymerization medium, and is variously used such as facilitating the dispersion of a crosslinking solution during surface crosslinking. And, residual moisture in the final product functions as an antistatic agent and a plasticizer, thus inhibiting the formation of very small superabsorbent polymer dust during the application process, and preventing superabsorbent polymer particles from being ground. However, in general, when water, even if a small amount, is added to superabsorbent polymer, stickiness of polymer surface increases by the water absorbed on the surface, and irreversible agglomeration between superabsorbent polymer particles may be generated. Such viscosity increase and agglomeration decreases processability such as increasing load during the preparation and application processes, and consequently, cause property deterioration and productivity decrease.

In the present invention, by additionally adding water to superabsorbent polymer in the above range to increase moisture content, water may function as a plasticizer to minimize physical damage of superabsorbent polymer, and high moisture content and high processability may be simultaneously satisfied, and thus, when water is introduced into superabsorbent polymer, uniform hydration is enabled without caking. Thus, in case the superabsorbent polymer is applied for final products such as a diaper, etc., for example, during the production process of a diaper, property degeneration due to the physical crushing of superabsorbent polymer caused by compression or strong air transfer may be minimized.

According to another embodiment of the present invention, it is preferable that the organic acid is included in the content of 0.001 to 5.0 parts by weight, based on 100 parts by weight of the superabsorbent polymer, but is not limited thereto.

If the organic acid is included in the above range, anti-caking of superabsorbent polymer may be improved, and hydrophobicity of the superabsorbent polymer surface due to the inclusion of the above described particles may be decreased. And, decrease in absorption under pressure (AUP) due to the use of the above described particles may be reduced.

If the content of the organic acid is greater than the above range, stickiness of superabsorbent polymer (SAP) surface may be generated, particle size may be adversely influenced during post treatment, and it is not economically preferable. And, anti-caking efficiency may significantly decrease. Meanwhile, if the content of the organic acid is less than the above range, aimed effect cannot be achieved.

It is preferable in terms of improvement in the absorption-related properties of the finally prepared superabsorbent polymer with improved anti-caking that the organic acid is citric acid.

According to one embodiment of the present invention, it is preferable that the polyhydric alcohol is included in the content of 0.01 to 5.0 parts by weight, based on 100 parts by weight of the superabsorbent polymer, but not limited thereto.

If the polyhydric alcohol is used together with water, it may reduce the amount of water substantially contained in superabsorbent polymer, thus slightly reducing decrease in centrifugal retention capacity (CRC). And, it may reduce absorption speed (vortex measurement value) and contribute to decrease in hydrophobicity. Finally, it may increase anti-caking of superabsorbent polymer, and prolong the maintenance period.

If the content of the polyhydric alcohol is greater than the above range, caking may be caused wherein superabsorbent polymers are attached to each other or form a lump. To the contrary, if the content is less than the above range, aimed effect cannot be achieved.

The polyhydric alcohol is preferably propylene glycol so as to improve the absorption-related properties of finally prepared superabsorbent polymer with improved anti-caking, and improve anti-caking of superabsorbent polymer finally prepared using particles having i) a BET specific surface area of 300 to 1500 m²/g, and ii) a porosity of 50% or more together.

DETAILED DESCRIPTION OF THE EMBODIMENTS

Hereinafter, the present invention will be explained in more detail through the examples. However, these examples are presented only as the illustrations of the invention, and the scope of the present invention is not limited thereby. The scope of the present invention is designated in the claims, and includes all the modifications within the meaning and scope equivalent to the description of the claims. And, "%" and "parts" indicating the contents in Examples and Comparative Examples below are based on mass, unless otherwise mentioned.

EXAMPLE

Preparation Example

Preparation of Superabsorbent Polymer(LK-501)

In a 2 L glass reactor surrounded by jacket in which heating medium precooled to 25° C. is circulated, 500 g of acrylic acid and 11 g of 0.5% IRGACURE 819 initiator diluted in acrylic acid (0.001 wt % based on the monomer composition) were mixed, a solution (solution A) of 26 g of 5% polyethyleneglycol diacrylate (PEGDA, molecular weight 400) diluted in acrylic acid was introduced, a solution (solution B) of 14 g of trimethylolpropane triacrylate comprising 9 mol % of 5% ethylene oxide (Ethoxylated-TMPTA, TMP(EO)9TA, M-3190, Miwon Specialty Chemicals) diluted in acrylic acid was introduced, and 800 g of 24% caustic soda solution (solution C) was slowly added dropwise and mixed. In the obtained water soluble ethylenically unsaturated monomers of sodium acrylate, the acrylic acid neutralization degree became 70 mol %.

When the two solutions were mixed, it was confirmed that the temperature of the mixed solution increased above 80° C. by neutralization heat, and then, waited until the temperature was cooled to 40° C., and when the reaction temperature reached 40° C., 54 g of 2% sodium persulfate solution diluted in water was introduced.

The solution was poured into a tray in the form of Vat (tray, width 15 cm×length 15 cm) installed in a square polymerization reactor equipped with a light irradiation device thereon, of which inside is preheated to 80° C., and light irradiation was conducted to photoinitiate. It was confirmed that gel was formed about 25 seconds after light irradiation, and that a polymerization reaction occurred simultaneously with foaming at about 50 seconds, and then, it was additionally reacted for 3 minutes, and the polymerized sheet was taken out and cut into a size of 3 cm×3 cm, and then, chopped using a meat chopper to prepare crumb.

The crumb was dried in an oven capable of transferring air volume upward and downward. Hot air of 180° C. was flowed from the lower part to the upper part for 15 minutes, and from the upper part to the lower part for 15 minutes so as to uniformly dry, and after drying, the moisture content of the dried substance became 2% or less.

After drying, the dried substance was ground with a grinder and sieved to select those of 150 to 850 µm size, thus preparing base resin. The prepared base resin has a centrifugal retention capacity of 36.5 g/g, and water soluble content of 12.5 wt %.

Thereafter, 100 g of the base resin was mixed with a crosslinking solution comprising 3 g of water, 3 g of methanol, 0.3 g of 1,3-propanediol, and 0.1 g of Aerosil 200, and surface crosslinked at 190° C. for 30 minutes and ground, and then, surface treated superabsorbent polymer with a particle diameter of 150 to 850 µm was obtained using a sieve.

Example 1

Preparation of Superabsorbent Polymer with Improved Anti-Caking (1) LK-501 prepared according to the Preparation Example was cut into a size of 5*5 mm and dried in a hot air dryer of 170° C. for 2 hours, ground with a pin mill grinder, and then, superabsorbent polymer with a particle diameter of 150 to 850 μm was obtained using a sieve.

(2) To the superabsorbent polymer, based on 100 wt % of the superabsorbent polymer, 0.025 wt % of porous superhydrophobic fine particles Aerogel(JIOS Company) were introduced and stirred, and then, in 4 wt % of water, 0.1 wt % of citric acid and 0.64 wt % of aluminium sulfate. 4-18$H_2O$, and 2 wt % of propylene glycol were dissolved and stirred with stirrer for 2 minutes to prepare superabsorbent polymer.

The average particle size of the porous superhydrophobic fine particles aerogel was 5 μm, BET specific surface area was 720 $m^2/g$, and water contact angle was 144°, and porosity was 95%.

The particle size of aerogel was measured by laser diffraction using HELOS(Helium-Neon Laser Optical System) according to ISO 13320. The BET specific surface area and porosity were measured with BET analyzer. The water contact angle was measured with contact angle analyzer (KRUSS DSA100), and specifically, a double-sided tape was attached to a flat glass plate, fine particles were coated thereon in a monolayer, and 5 μl of ultrapure water was put on the monolayer and then positioned in the form of drops, and at this time, the angle made by the water drop and glass plate was measured repeatedly 4 times, and the mean value was calculated.

Thereafter, the prepare superabsorbent polymer was aged at 26~95° C. for 30 minutes, at a stirring velocity of 30 rpm, using kitchen aid as a stirrer, thus preparing final superabsorbent polymer with improved anti-caking.

Comparative Example 1

Preparation of Superabsorbent Polymer (1) LK-501 prepared according to the Preparation Example was cut into a size of 5*5 mm and dried in a hot air dryer of 170° C. for 2 hours, ground with a pin mill grinder, and then, superabsorbent polymer with a particle diameter of 150 to 850 μm was obtained using a sieve.

(2) To the superabsorbent polymer, based on 100 wt % of the superabsorbent polymer, 0.015 wt % of hydrophilic fine particles Aerosil-200 (manufactured by Evonic Degussa Corporation) were mixed by dry mixing, and then, stirred with a stirrer.

The average compression density of the hydrophilic fine particles is 50 g/L, and the BET specific surface area is 200±25 $m^2/g$. The information on the properties of the Aerosil-200 was provided by the manufacturing company.

Comparative Example 2

Superabsorbent Polymer

Superabsorbent polymer(GS-301N, manufactured by LG corporation) dry treated with 0.015 wt % of hydrophilic fine particles Aerosil-200 (manufactured by Evonic Degussa Corporation) was used.

Comparative Example 3

Superabsorbent Polymer

Superabsorbent polymer(GS-4800N, manufactured by LG corporation) dry treated with 0.0007 wt % of hydrophilic fine particles Aerosil-200 (manufactured by Evonic Degussa Corporation) was used.

Comparative Example 4

Superabsorbent Polymer

Superabsorbent polymer(GS-3100N, manufactured by LG corporation) wet treated with 0.001 wt % of hydrophilic fine particles DM-30S (manufactured by Tokuyama Corporation) was used.

Experimental Example 1

Anti-Caking Test

For the superabsorbent polymers prepared in Example 1 and Comparative Examples 1 to 4, anti-caking test was conducted.

1) The mass (W1) of a petri dish with a diameter of 9 cm was measured.

2) To the petri dish, 2±0.01 g of the superabsorbent polymers (Total mesh) according to Example 1 and Comparative Examples 1 to 4 were sampled and uniformly dispersed.

3) The petri dish where the superabsorbent polymer is dispersed was put in a thermo-hygrostat with a temperature of 40° C. and humidity of 80% RH, and allowed to stand for 10 minutes.

4) After standing for 10 minutes, the petri dish was taken out, turned upside down on a A4 paper, and was allowed to stand for 5 minutes.

5) After 5 minutes, the mass (S1) of superabsorbent polymer separated from the dish and dropped on the bottom was measured and recorded.

6) Thereafter, the mass (S2) of the petri dish where superabsorbent polymer remains was measured and recorded.

7) Anti-caking efficiency was calculated by the following Mathematical Formula 1, and the results are shown in the following Table 1.

[Mathematical Formula 1]

$$\text{Anti-caking efficiency}(\%) = \left(\frac{S1}{(S2-W1)+S1}\right) \times 100$$

(wherein, S1 is the mass of polymer separated from the petri dish after aging, W1 is the mass of the petri dish, and S2 is the mass of polymer remaining in the petri dish after aging)

TABLE 1

|  | anti-caking efficiency |
|---|---|
| Example 1 | 99.1 |
| Comparative Example 1 | 73.7 |
| Comparative Example 2 | 0.94 |

TABLE 1-continued

| | anti-caking efficiency |
|---|---|
| Comparative Example 3 | 82.1 |
| Comparative Example 4 | 83.0 |

From the above results, it was confirmed that Example 1 has superior anti-caking to Comparative Example 1. As shown in FIG. 1, in the case of the superabsorbent polymer prepared according to Example 1, when maintained under conditions of temperature of 40° C. and humidity of 80% RH for 10 minutes, caking between superabsorbent polymers did not occur.

However, in the case of the superabsorbent polymer prepared in Comparative Example 1, superabsorbent polymers dropped from the petri dish while caking with each other. Although anti-caking efficiency was as high as 73.4% on the numerical value, caking occurred.

In addition, even compared to the existing superabsorbent polymers with anti-caking of Comparative Examples 2 to 4, the effect of Example 1 was most remarkable.

It was analyzed that the superabsorbent polymer of Comparative Example 2 has anti-caking efficiency of 0% under the same conditions, and the superabsorbent polymers of Comparative Examples 3 and 4 have anti-caking efficiencies of about 80%.

As shown in FIG. 4 and FIG. 5, FIG. 9 and FIG. 10, in the case of the superabsorbent polymers of Comparative Examples 3 and 4, although the amounts of superabsorbent polymers dropped on the petri dish were large, caking occurred.

These results show that the superabsorbent polymer of Example 1 of the present invention, which is surface-treated with the particles having the properties of i) and ii), multivalent metal salt, polyhydric alcohol and organic acid, has improved anti-caking efficiency of 99%, indicating that anti-caking is greatly improved compared to the prior art.

What is claimed is:

1. A method for preparing superabsorbent polymer, comprising:

introducing water, particles having a BET specific surface area of 500 to 1500 m$^2$/g and a porosity of 50% or more, and one or more selected from the group consisting of multivalent metal salts, organic acid and polyhydric alcohol into a superabsorbent polymer to prepare a hydrated superabsorbent polymer; and aging the hydrated superabsorbent polymer.

2. The method for preparing superabsorbent polymer according to claim 1, wherein the aging is conducted at 26 to 95° C.

3. The method for preparing superabsorbent polymer according to claim 1, wherein the aging is conducted for 1 to 120 minutes.

4. The method for preparing superabsorbent polymer according to claim 1, wherein the particles are included in the content of 0.001 to 2.0 parts by weight, based on 100 parts of the superabsorbent polymer.

5. The method for preparing superabsorbent polymer according to claim 1, wherein the water is included in the content of 1.0 to 10.0 parts by weight, based on 100 parts by weight of the superabsorbent polymer and particles.

6. The method for preparing superabsorbent polymer according to claim 1, wherein the organic acid is included in the content of 0.001 to 5.0 parts by weight, based on 100 parts by weight of the superabsorbent polymer.

7. The method for preparing superabsorbent polymer according to claim 1, wherein the polyhydric alcohol is included in the content of 0.01 to 5.0 parts by weight, based on 100 parts by weight of the superabsorbent polymer.

8. The method for preparing superabsorbent polymer according to claim 1, wherein the organic acid is citric acid.

9. The method for preparing superabsorbent polymer according to claim 1, wherein the polyhydric acid is propylene glycol.

10. The method for preparing superabsorbent polymer according to claim 1, wherein the particle has a particle size of 2 nm to 50 μm.

11. The method for preparing superabsorbent polymer according to claim 1, wherein the particle has super hydrophobicity with a water contact angle of 125° or more.

12. The method for preparing superabsorbent polymer according to claim 1, wherein the particle has a particle size of 2 nm to 50 μm and super hydrophobicity with a water contact angle of 125° or more.

13. The method for preparing superabsorbent polymer according to claim 1, wherein the particle is one or more selected from the group consisting of silica ($SiO_2$), alumina, carbon, and titania ($TiO_2$).

14. The method for preparing superabsorbent polymer according to claim 1, wherein the particle is silica ($SiO_2$).

15. The method for preparing superabsorbent polymer according to claim 1, wherein the particle has a BET specific surface area of 600 m$^2$/g to 1500 m$^2$/g.

16. The method for preparing superabsorbent polymer according to claim 1, wherein the particle has super hydrophobicity with a water contact angle of 140° or more.

17. The method for preparing superabsorbent polymer according to claim 16, wherein the particle has super hydrophobicity with a water contact angle of 145° or more.

18. The method for preparing superabsorbent polymer according to claim 1, wherein the particle has a porosity of 90% or more.

19. The method for preparing superabsorbent polymer according to claim 1, wherein the aging comprises stirring at 5-1500 rpm at a temperature of 26-95° C. for 1-120 minutes.

* * * * *